US00PP31719P3

(12) United States Plant Patent
Contreras

(10) Patent No.: US PP31,719 P3
(45) Date of Patent: May 5, 2020

(54) ***COTONEASTER* PLANT NAMED 'EMERALD SPRITE'**

(50) Latin Name: ***Cotoneaster* x *suecicus***
Varietal Denomination: Emerald Sprite

(71) Applicant: Oregon State University, Corvallis, OR (US)

(72) Inventor: Ryan N. Contreras, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 3 days.

(21) Appl. No.: 16/350,082

(22) Filed: Sep. 21, 2018

(65) Prior Publication Data

US 2020/0100412 P1 Mar. 26, 2020

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/00; A01H 5/02
See application file for complete search history.

(56) References Cited

PUBLICATIONS

Rothleutner et al., "Screening *Cotoneaster* for Resistance to Fire Blight by Artificial Inoculation," *HortScience,* 49, 1480-1485, 2014.

*Primary Examiner* — Kent L Bell
(74) *Attorney, Agent, or Firm* — Klarquist Sparkman, LLP

(57) ABSTRACT

'Emerald Sprite' is a new *Cotoneaster* cultivar with a highly compact, mounding habit, extremely dense foliage, short internodes, and improved fire blight resistance.

7 Drawing Sheets

ACKNOWLEDGMENT OF GOVERNMENT SUPPORT

This invention was made with government support under 58-1230-3-501 awarded by Agricultural Research Service, United States Department of Agriculture. The government has certain rights in the invention.

Botanical denomination: *Cotoneaster* x *suecicus.*
Variety designation: 'Emerald Sprite'.

BACKGROUND

The present invention relates to a new and distinct cultivar of *Cotoneaster* plant, botanically known as *Cotoneaster* x *suecicus* and hereinafter referred to as 'Emerald Sprite'.

The new *Cotoneaster* plant is a result of a breeding program directed by the inventor at Oregon State University, Corvallis, Oreg. (US) to develop new cultivars of *cotoneasters* that are resistant to fire blight caused by the pathogen *Erwinia amylovora*, are compact, and perform well in nursery production and landscapes.

'Emerald Sprite' originated as an open-pollinated seedling collected from *Cotoneaster* x *suecicus* 'Coral Beauty' (seed parent, unpatented) during 2011 that was pollinated by an unknown pollen parent. It was originally accessioned and evaluated as H2011-02-001. 'Emerald Sprite' was grown in containers during 2012 for observation and selected for propagation in 2013. It was propagated by stem cuttings that rooted easily with hormone treatment under mist in a glasshouse located on Oregon State University's main campus at 2801 SW Campus Way, Corvallis, Oreg. Clones produced from serial asexual propagation have demonstrated the stability of its traits from 2013 through 2018. The original plant was left outside unprotected in a #3 container during winter 2013-14 and was killed during temperatures that reached 0° F. Replicates produced from stem cuttings were included in a glasshouse study to evaluate fire blight resistance of hybrids and parents during 2014. Plants were inoculated on Apr. 28, 2014 with a virulent strain (Ea153) of *Erwinia amylovora* by bisecting the two youngest leaves on vigorously growing shoots according to Rothleutner et al. (2014). None of the plants of this accession exhibited disease symptoms (0% shoot infection). 'Coral Beauty' had 11.1% mean shoot infection during that evaluation.

SUMMARY

Plants of the new *Cotoneaster* have not been observed under all possible environmental conditions. The phenotype may vary somewhat with variations in environment and cultural practices such as temperature and light intensity without any variance in genotype.

The following traits have been repeatedly observed and are determined to be unique to 'Emerald Sprite'. Collectively, these traits distinguish 'Emerald Sprite' from other available *cotoneasters.*

1. Highly compact growth form with a clumping growth habit, as opposed to the more standard creeping habit.
2. Resistance to fire blight.
3. Extremely glossy, dark green leaves adaxially.
4. Excellent container production performance.
5. Short internodes.
6. More vigorous and faster production than other dwarf cultivars such as 'Tom Thumb' (unpatented).

Compared to its female parent, *Cotoneaster* x *suecicus* 'Coral Beauty', plants of 'Emerald Sprite' are easily distinguishable based on the following traits:

1. 'Emerald Sprite' has a more regular growth form.
2. 'Emerald Sprite' has a more compact habit.
3. 'Emerald Sprite' has fire blight resistance.
4. 'Emerald Sprite' requires little or no pruning during production to yield salable plants.

The foregoing and other objects and features of the new variety will become more apparent from the following detailed description, which proceeds with reference to the accompanying figures.

BRIEF DESCRIPTION OF THE DRAWINGS

The accompanying photographs illustrate the new 'Emerald Sprite' cultivar in color as nearly true as it is reasonably possible to make the same in color illustrations of this nature. The plants were grown outside in full sun in containers and in the landscape in Corvallis, Oreg., USA.

DETAILED DESCRIPTION

Figure 1:
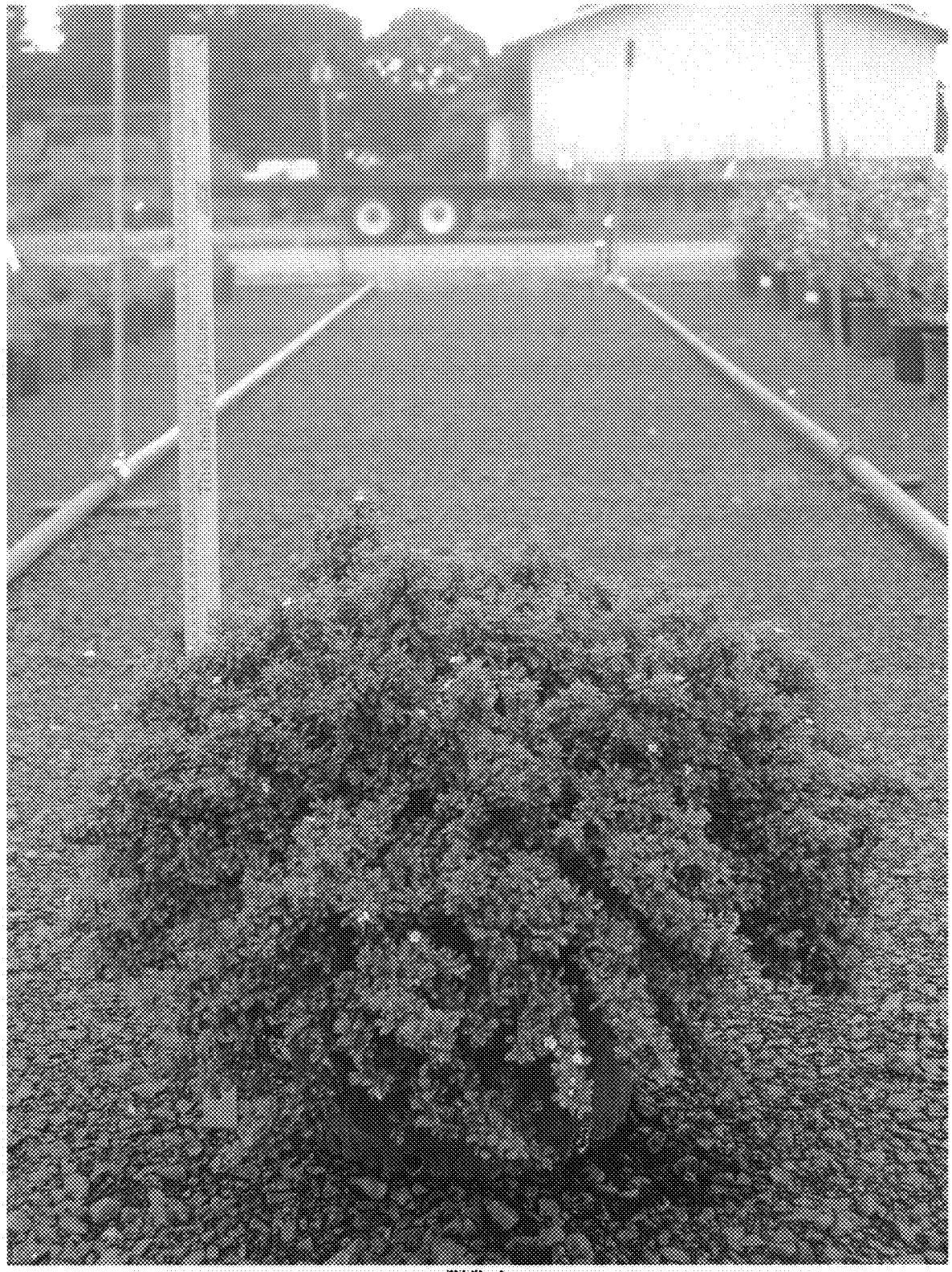
FIG. 1—Illustrates a typical mature four-year old plant growing in a container. The mounding habit is clearly visible. The scale included is 92 cm tall, which helps illustrate the compact nature of 'Emerald Sprite'.
Figure 2:
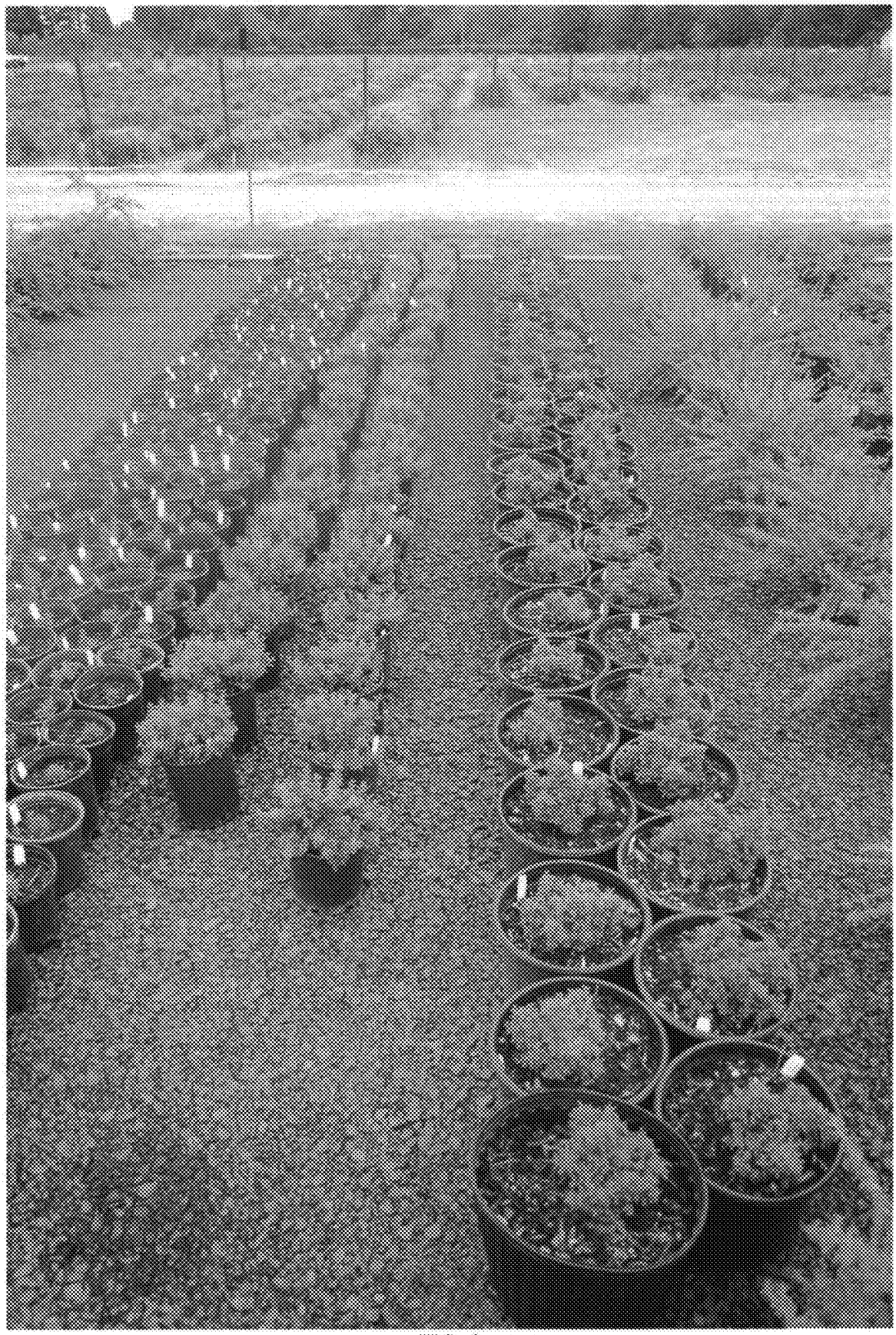
FIG. 2—Illustrates the uniform nature of clones produced from stem cuttings. Presented are two groups propagated at different times. An older group (left) and younger group (right) clearly both exhibit the characteristic mounding, compact habit.
Figure 3:
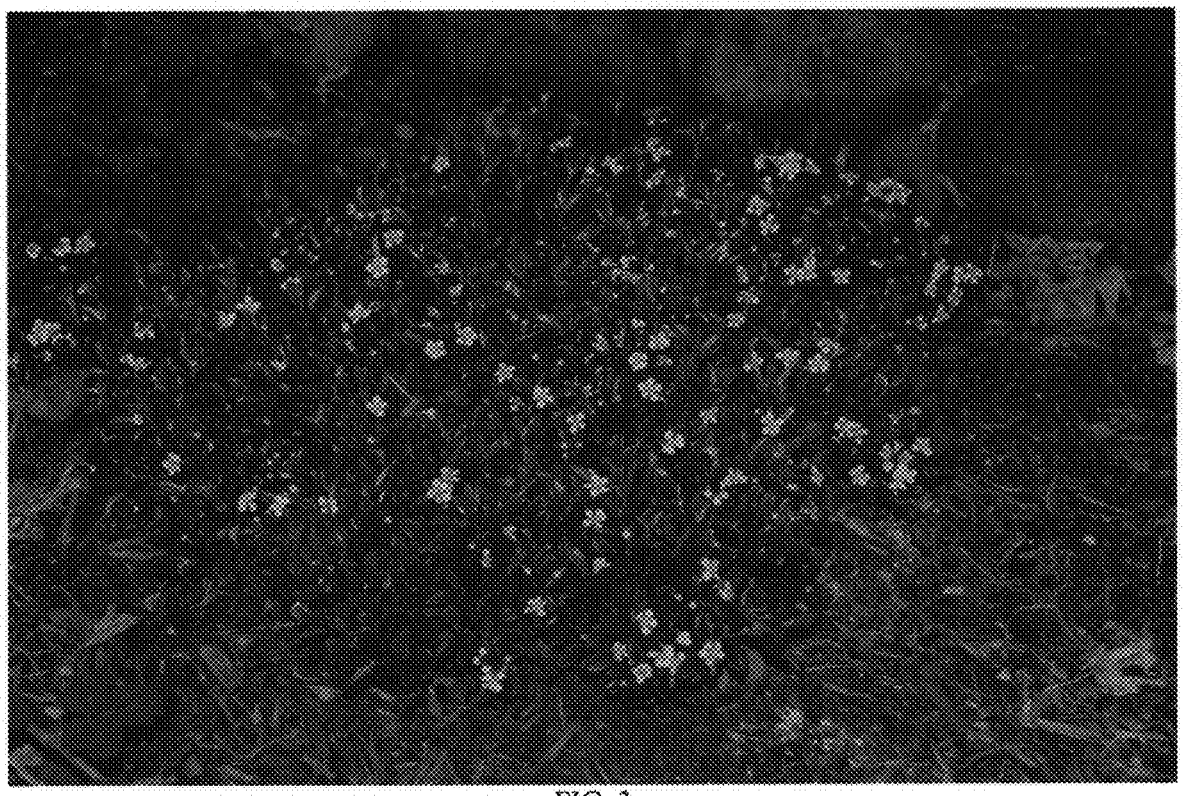
FIG. 3—Illustrates the consistent performance in the landscape where it maintains its mounding habit and moderate to heavy production of flowers that are pink in bud and open to white.
Figure 4:
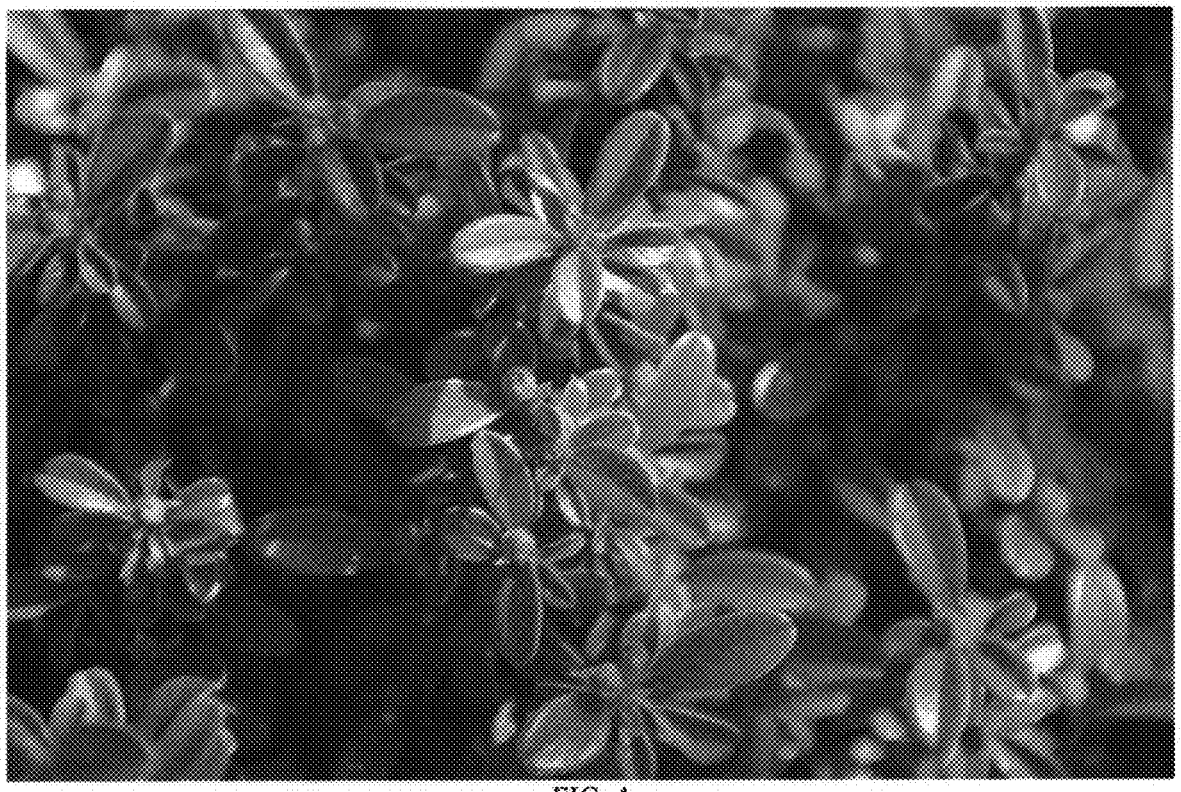
FIG. 4—Illustrates the attractive pink floral buds prior to opening.
Figure 5:
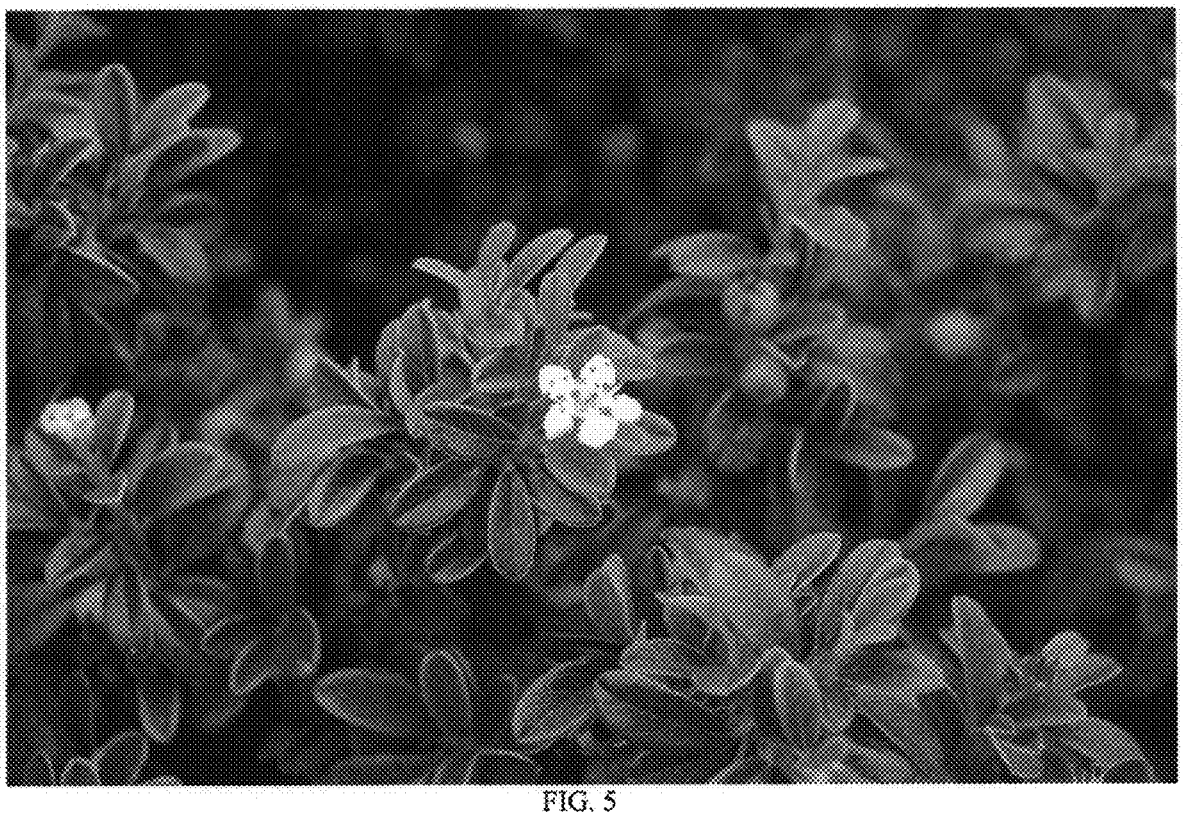
FIG. 5—Illustrates the near-pure white flowers.
Figure 6:
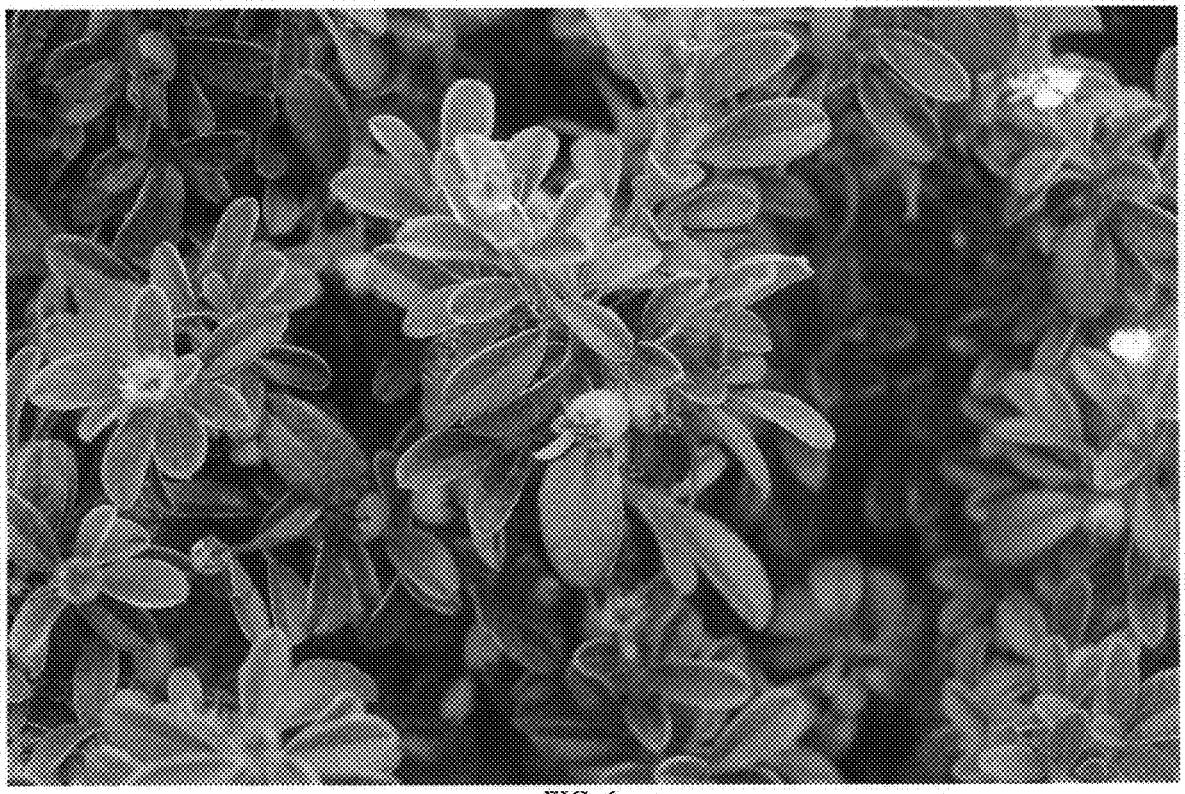
FIG. 6—Illustrates the approximate color of fruit.
Figure 7:
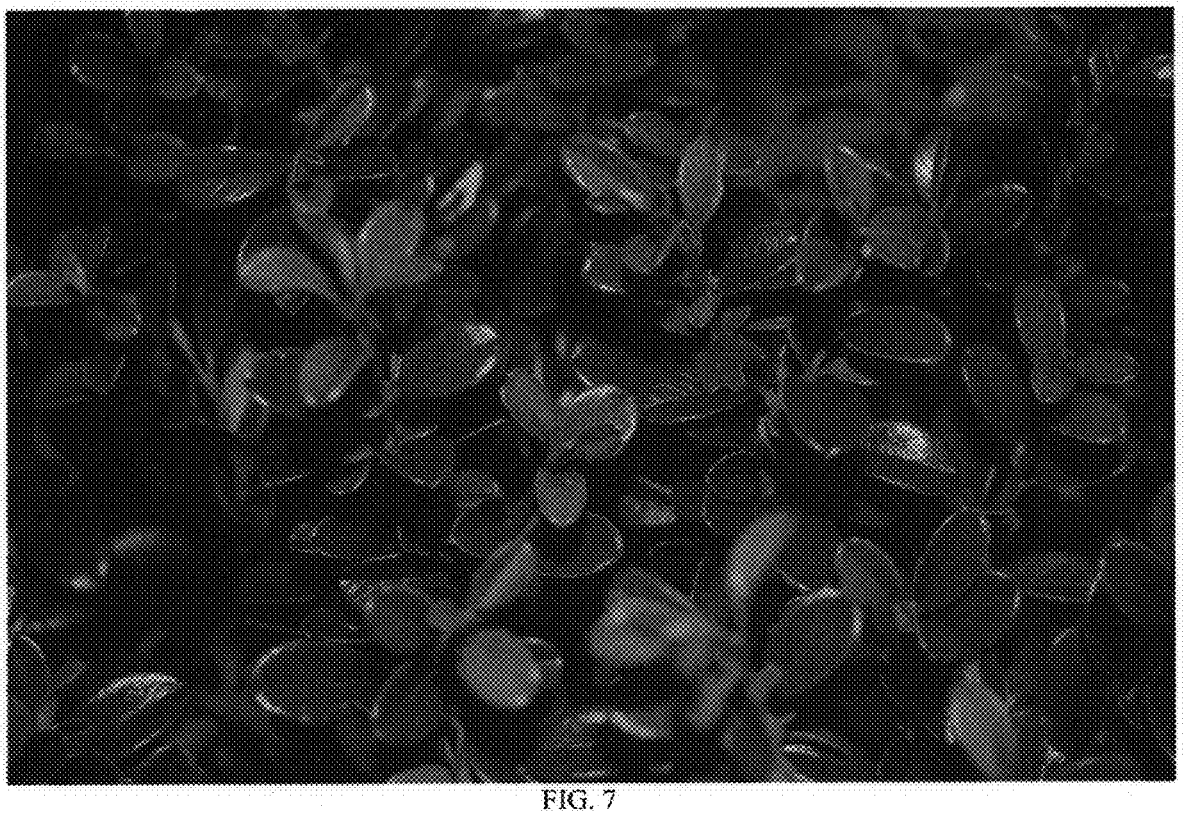
FIG. 7—Illustrates the glossy leaves as well as color of new foliage and stems.

The following is a detailed description while observing mature plants of the new cultivar following the rooting of stem cuttings. Such plants ranged between two and five years of age and were found to have consistent morphology with the exception of size (younger plants are smaller). Plants were observed growing outdoors in full sun in Corvallis, Oreg., USA. Color terminology is in accordance to The R.H.S. Colour Chart (fifth edition) of The Royal Horticultural Society, London, 2007.

Classification:

*Botanical name.*—*Cotoneaster* x *suecicus.*
*Common name.*—*Cotoneaster.*
*Variety name.*—'Emerald Sprite'.

Parentage: Open-pollinated seedling collected from *Cotoneaster* x *suecicus* 'Coral Beauty', which was pollinated by an unknown pollen parent—likely a self-pollination.

Plant description:

*Growth habit.*—Cushion-like, low growing with somewhat upright stems.
*Height at maturity.*—31 cm.
*Width at maturity.*—74 cm.

Stem:

*Stem shape.*—Round.
*Length.*—Variable lateral branch length from 1 cm to 4 cm.
*Diameter.*—1.5 mm.
*Mature stem texture.*—Pubescent, sparsely sericeous.
*Internode length.*—About 2 mm.
*Mature stem color.*—Greyed-Brown Group 199B.
*Immature stem color.*—Yellow-Green Group N144C.

Leaves:

*Type.*—Evergreen to semi-evergreen.
*Arrangement.*—Alternate.
*Shape.*—Elliptic, keeled.
*Veins.*—Pinnate.
*Mature leaf texture.*—Glabrous adaxially, light pubescent and reticulate abaxially.
*Base.*—Cuneate to nearly rounded.
*Apex.*—Retuse.
*Margin.*—Entire.
*Mature leaf size.*—1.7 cm long×0.8 cm wide.
*Immature leaf color.*—Greyed-Purple Group 183A.
*Mature leaf color.*—Adaxial surface — Green Group N134A, Abaxial surface — Green Group 138B. Venation is pinnate. Color does not deviate markedly from the base leaf color either adaxially or abaxially. Adaxial venation — Green Group N134A, abaxial venation — Green Group 138B.
*Petiole length.*—0.4 cm.
*Petiole diameter.*—0.65 mm.
*Petiole color.*—Yellow-Green Group N144C.

Inflorescence:

*Number of flowers per inflorescence.*—Solitary or 2-5.
*Diameter.*—0.8 to 1.1 cm.
*Length.*—About 1 cm.
*Type.*—Solitary or corymb.
*Number per branch.*—1.
*Peduncle length.*—Up to 5 mm.
*Peduncle diameter.*—About 1 mm.
*Peduncle color.*—Greyed-Purple Group 183A.
*Flowering season.*—May to June.
*Longevity.*—Individual flowers last 10 to 14 days.

Flower:

*Bud color.*—Red-Purple Group 68A to N57A.
*Bud shape.*—Ovoid.
*Bud length.*—6 mm.
*Bud width.*—2.5 mm.
*Petals.*—Five petals, White Group NN155C adaxially and abaxially.
*Diameter.*—1 cm.
*Depth.*—3 mm.
*Fragrance.*—None.
*Petal shape.*—Rhombic-obdeltoid.
*Petal length.*—4.5 mm.
*Petal width.*—4 mm.
*Petal apex.*—Rounded to subacute.
*Petal margin.*—Entire.
*Petal base.*—Rounded.
*Petal surface texture.*—Glabrous abaxially and adaxially.
*Sepal shape.*—Deltoid.
*Sepal number.*—5.
*Sepal length.*—1.3 mm.
*Sepal width.*—1.3 mm.
*Sepal apex.*—Acute.
*Sepal margin.*—Entire and ciliate-puberulent.

*Sepal surface texture*.—Pubescent adaxially, glabrous abaxially.
*Sepal color*.—Abaxial and adaxial surfaces are Yellow-Green Group N144C.
*Pistil number*.—2-3.
*Style length*.—3 mm.
*Pistil width*.—About 0.5 mm.
*Pistil color*.—Yellow-White Group 158D.
*Ovary shape*.—Ovoid.
*Ovary length*.—1 mm.
*Ovary width*.—0.5 mm.
*Ovary color*.—Yellow-Green Group 150C.
*Stamen number*.—20.
*Filament length*.—2.8 mm.
*Filament diameter*.—Tapering from 0.5 mm toward apex to 0.75 mm at base.
*Filament color*.—Green-White Group 157D.
*Filament shape*.—Round.
*Anther diameter*.—0.5 mm.
*Anther length*.—0.75 mm.
*Anther color at dehiscence*.—Greyed-Purple Group 187A.
*Pollen amount*.—Copious.
*Pollen color*.—8D.

Fruit/seed:
*Fruit*.—Generally obovate, 0.5 cm diameter and 0.5 cm long, base color is Greyed-Red Group 180C with a somewhat irregular coloration and generally lighter than other cultivars with green undertones.

Propagation and production: 2.5 cm softwood tip cuttings treated with 1000 ppm auxin and set in 3 parts perlite: 1 part peat in a community flat under intermittent mist and bottom heat rooted 90% in 28 days. 'Emerald Sprite' plants were put through a production schedule that indicates plants can be propagated and produce a finished trade gallon container in approximately 9-months.

Disease and insect resistance: 0% shoot infection following inoculation with a virulent strain of *Erwinia amylovora* (Ea153), whereas its seed parent, *Cotoneaster* x *suecicus* 'Coral Beauty' had 11.1% mean shoot infection during the same evaluation.

I claim:

1. A new and distinct cultivar of *Cotoneaster* plant as illustrated and described.

* * * * *